(12) United States Patent
Chabloz

(10) Patent No.: US 8,870,969 B2
(45) Date of Patent: Oct. 28, 2014

(54) PROSTHESIS FOR A LOWER LIMB

(75) Inventor: Pierre Chabloz, Saint Georges de Commiers (FR)

(73) Assignee: Otto Bock Healthcare GmbH, Duderstadt (DE)

( * ) Notice: Subject to any disclaimer, the term of this patent is extended or adjusted under 35 U.S.C. 154(b) by 110 days.

(21) Appl. No.: 13/315,827

(22) Filed: Dec. 9, 2011

(65) Prior Publication Data

US 2012/0150318 A1    Jun. 14, 2012

(30) Foreign Application Priority Data

Dec. 9, 2010 (FR) ...................................... 10 04800

(51) Int. Cl.
*A61F 2/64* (2006.01)
*A61F 2/50* (2006.01)
*A61F 2/60* (2006.01)

(52) U.S. Cl.
CPC ............ *A61F 2/64* (2013.01); *A61F 2002/5038* (2013.01); *A61F 2002/5006* (2013.01); *A61F 2002/607* (2013.01)
USPC .......................................................... 623/44

(58) Field of Classification Search
CPC combination set(s) only.
See application file for complete search history.

(56) References Cited

U.S. PATENT DOCUMENTS

| 5,387,246 | A | * | 2/1995 | Phillips ............................. 623/56 |
| 5,645,590 | A | * | 7/1997 | van de Veen .................... 623/44 |
| 7,278,522 | B2 | | 10/2007 | Reinhardt et al. |
| 2007/0050044 | A1 | | 3/2007 | Haynes et al. |
| 2007/0162152 | A1 | | 7/2007 | Herr et al. |

FOREIGN PATENT DOCUMENTS

| EP | 1 417 942 A2 | 5/2004 |
| EP | 1 598 573 A1 | 11/2005 |
| RU | 1801416 A1 * | 3/1993 ................ A61F 2/62 |

* cited by examiner

*Primary Examiner* — David H Willse
(74) *Attorney, Agent, or Firm* — Holland & Hart

(57) ABSTRACT

A prosthesis for a lower limb includes an element for receiving a thigh stump fitted on a support part, a leg assembled on the support part by a pivot link forming a knee joint to enable flexion or extension of the leg with respect to the element for receiving, and an absorbing system to absorb the flexion or extension efforts. The absorbing system is fitted on the one hand on the pin of the pivot link and on the other hand on a first end of a rocker pivotally mounted on the leg, and a rod is fitted on the one hand on a second end of the rocker and on the other hand on the support part.

19 Claims, 5 Drawing Sheets

PROSTHESIS FOR A LOWER LIMB

BACKGROUND OF THE INVENTION

The invention relates to a prosthesis for a lower limb comprising:
- an element for receiving a thigh stump fitted on a support part,
- a leg assembled on said support part by a pivot link forming a knee joint to enable flexion or extension of the leg with respect to the element for receiving,
- an absorbing system to absorb the flexion or extension efforts.

STATE OF THE ART

Persons having a lower limb amputated between the knee and the hip have already been offered the possibility of being able to ski again.

In a first approach, amputated persons skied on a single leg and were equipped with crutches provided with small skis at their ends for them to be able to keep their balance.

In a second approach, it was proposed to give amputated persons the possibility of skiing on two lower limbs with a prosthetic material performing functions close to those of a real lower limb under particular conditions, such as the triple flexion position (hip, knee, ankle) with an absorber enabling the contours of a ski slope to be absorbed.

Articulated prostheses for the lower limb comprising an element for receiving a thigh stump of a patient thus exist. The element can then be fitted onto a leg by a pivot link the pin of which forms a knee joint to enable flexion or extension of the leg with respect to the element. A jack enables the flexion or extension efforts to be absorbed.

In the example of FIGS. 1 and 2, a support part 1, on which the element for receiving 6 are fitted, is itself fitted on leg 3 by a pivot link 2 so as to form a knee joint. Jack 4 is fitted on the one hand on a front part of leg 3 (part facing a foot 5), and on the other hand on a rear part (zone at the level of which the angle α closes in case of flexion) of support part 1.

FIG. 1 illustrates the position of the prosthesis in flexion with an angle α of 155 degrees between leg 3 and element for receiving 6 at the level of the flexion. FIG. 2 illustrates an angle α of 110 degrees. With angle α at 155 degrees, the force Fjack exerted by jack 4 is about 2500N whereas at 110 degrees the force Fjack exerted by the same jack 4 is about 5100N. The more the prosthesis is flexed, the more the jack will in fact have difficulty in counteracting the flexion, and the user then finds him/herself without a shock absorbing system which may lead to breaking at the level of the joint. Furthermore, the convenience of use of the prosthesis is thereby greatly impaired.

OBJECT OF THE INVENTION

The object of the invention is to provide a more solid prosthesis that has a behavior close to that of a valid leg.

This object tends to be achieved by the appended claims and in particular by the fact that the absorbing system is fitted on the one hand on the pin of the pivot link and on the other hand on a first end of a rocker pivotally fitted on the leg, and in that a rod is mounted on the one hand on a second end of the rocker and on the other hand on the support part.

Such a fitting also results in a better stabilization of a user of the prosthesis when skiing.

BRIEF DESCRIPTION OF THE DRAWINGS

Other advantages and features will become more clearly apparent from the following description of particular embodiments of the invention, given for non-restrictive example purposes and represented in the appended drawings in which.

DESCRIPTION OF PREFERRED EMBODIMENTS

The prosthesis described in the following differs from the prosthesis according to the prior art in that its particular assembly enables the efforts of the absorbing system to be limited.

What is meant by lower limb of a person is a thigh, a knee and a foot. The thigh is the part situated between the hip and the knee, and the leg is the part situated between the knee and the instep.

Figure 1:
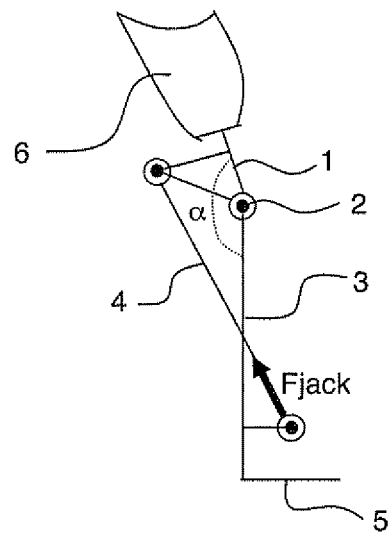
FIGS. 1 and 2 schematically illustrate devices of the prior art in distinct positions.
Figure 2:
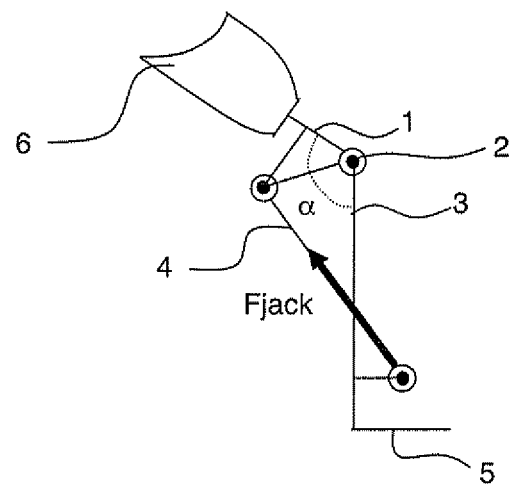
Figure 3:
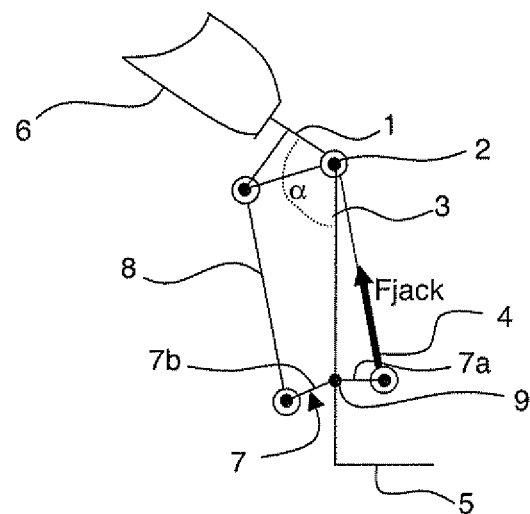
FIG. 3 schematically illustrates a particular device according to the invention.

FIG. 3 schematically illustrates a prosthesis for a lower limb comprising element for receiving 6 a thigh stump fitted on a support part 1. A leg 3 is assembled on said support part 1 by means of a pivot link 2 forming a knee joint to enable flexion or extension of leg 3 with respect to the element for receiving 6 (at angle α, in FIG. 3). A absorbing system 4, enabling the flexion or extension efforts to be absorbed, is fitted on the one hand on the pin of pivot link 2 and on the other hand on a first end of a rocker 7 pivotally mounted on leg 3. A rod 8 is fitted on the one hand on a second end of rocker 7 and on the other hand on support part 1 so as to transmit the pivoting movement of the support part around the pin of pivot link 2 to the rocker to solicit the absorbing system more or less.

When support part 1 pivots around the pin of pivot link 2, rod 8 transmits the pivoting to the rocker, thereby transmitting the movement to the absorbing system 4 decreasing, or increasing, the distance separating the assembly point of absorbing system on rocker 7 from the assembly point at the level of the pin (also called "axis" in the domain) of pivot link 2. In other words, the smaller the angle α is, the more the absorbing system will be compressed, i.e. in case of flexion, the distance separating the assembly point of said system 4 on the rocker will move towards the pin of pivot link 2. Naturally, the respective assembly points of absorbing system 4 and of rod 8 at the level of the rocker are advantageously situated at the ends of rocker 7 arranged on each side of swivel pin 9 of rocker 7. Furthermore, in the particular implementation, the assembly point of rod 8 at the level of support part 1 is situated on the same side as the assembly point of rod 8 on rocker 7.

In other words, rocker 7 can comprise two branches 7a, 7b on each side of its swivel pin 9. A first branch 7a is directed towards a first surface called front surface of the prosthesis (the front surface is in fact the surface of the prosthesis facing a foot 5). A second branch 7b is directed towards a second surface, opposite the first surface, and called rear surface of the prosthesis (the rear surface of the prosthesis corresponds to the rear face of a lower limb, i.e. the face which will enable element for receiving 6 to be moved towards leg 3 by flexion). In the particular example of FIG. 3, absorbing system 4 is fitted on first branch 7a of rocker 7 at an end of first branch 7a proximal to the front surface of the prosthesis. Rod 8 is fitted on second branch 7b of rocker 7, at an end of rocker 7 proximal to the rear surface of the prosthesis, and fitting of rod 8 at the level of support part 1 is performed at the level of the rear surface of the prosthesis.

Figure 4:
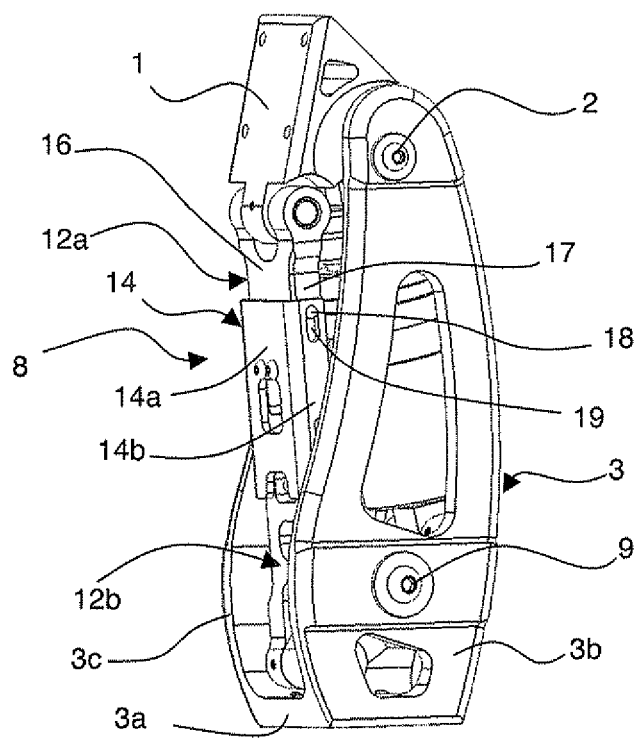
FIG. 4 illustrates a view in three dimensions of the leg and of the support part in the flexion position.
Figure 5:
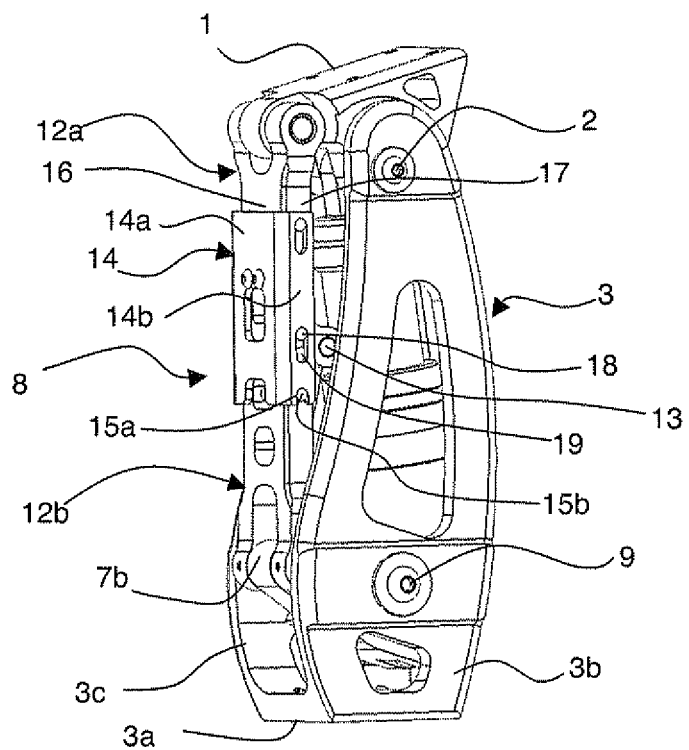
FIG. 5 illustrates a view in three dimensions of the leg and of the support part in the extension position.

FIGS. 4 and 5 illustrate a particular embodiment. According to this particular embodiment, leg 3 can have a monoblock main part comprising a base 3a connecting two uprights 3b, 3c substantially parallel to one another. At the end of leg 3 distal from base 3a, a pin can be fitted so as to connect the two uprights 3a, 3b, preferably perpendicularly. This pin can be fixed with respect to uprights 3b, 3c. Support part 1 is pivotally mounted on this pin, designed to form pivot link 2 referred to in the foregoing.

Figure 6:
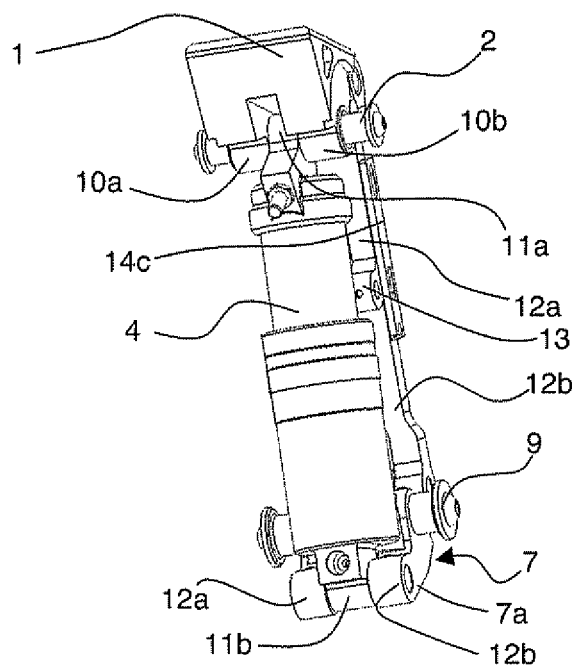
FIG. 6 illustrates a view in three dimensions of the leg and of the support part without the main body of the leg.

Support part 1 can be a part which is for example monoblock, comprising a first assembly zone designed to receive the pin of pivot link 2 and a second assembly zone designed to receive a pin for fixing one end of rod 8. As illustrated in FIG. 6 in which the main body of leg 3 has been removed for the sake of clarity, the first assembly zone can comprise two sections 10a, 10b each comprising a bore, the bores of said sections 10a, 10b being coaxial. The two sections 10a, 10b are separated by an empty space, between the two sections 10a, 10b, designed to receive one end of absorbing system 4 equipped with a first assembly part 11a comprising a bore designed to receive the pin of pivot link 2. Thus, in the assembled position, the pin of pivot link 2 passes through the two bores of sections 10a, 10b of support part 1, and the bore of first assembly part 11a.

In FIGS. 4 and 5, the pin of pivot link 2 of the joint is fixed at the level of the two uprights 3b, 3c of leg 3, and support part 1 and absorbing system 4 are mounted with swivelling/rotation on the pin of pivot link 2 between the two uprights 3b, 3c.

Figure 7:
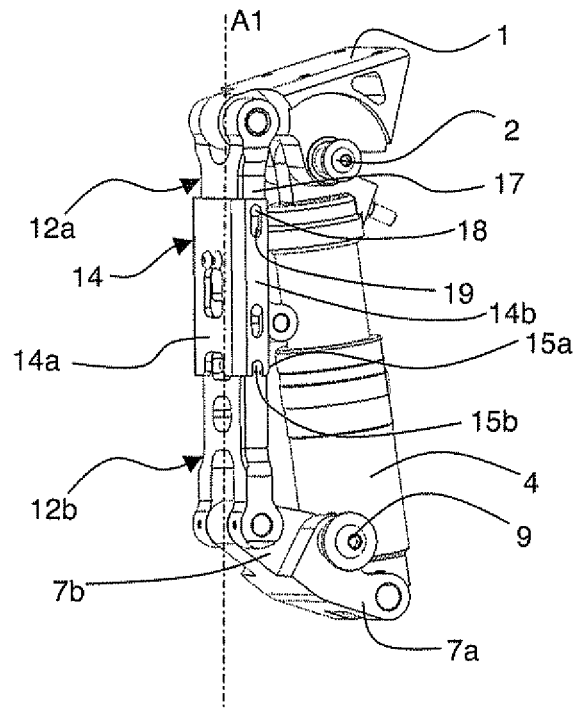
FIG. 7 illustrates a different view of FIG. 6.

Rocker 7 can be secured to said to uprights 3b, 3c by swivel pin 9 between the two uprights 3b, 3c, and preferably in proximal manner to base 3a, (FIGS. 4 to 6). Rocker 7 then comprises two distal ends formed by branches 7a, 7b visible in FIG. 7, a first end being directed towards the front part of leg 3 and a second end being directed towards the rear part of leg 3. The first end is designed for fitting of absorbing system 4. Absorbing system 4 can be fitted on this first end by means of an associated pivot link. In the particular example of FIG. 6, at its first end, the rocker comprises two sections of rocker 12a, 12b separated by an empty space, forming a Y. Between the two sections of rocker 12a, 12b, a second assembly part 11b (FIG. 6) of absorbing system 4 is inserted in such a way that a common pin can be inserted in the bores respectively formed at the level of the two sections 12a, 12b of rocker and of second assembly part 11b.

The second end of rocker 7 is designed for fitting of rod 8. Rod 8 can be fitted on this second end by means of a pin forming a pivot link. In other words, at its second end, the rocker can comprise a bore receiving a pin on which rod 8 can be fitted.

Opposite its fitting point on rocker 7, rod 8 can be mounted pivoting around a pin arranged at the rear (rear surface of the prosthesis) of support part 1, said pin being able to be fixed with respect to support part 1. In FIGS. 4 and 5, rod 8 can comprise two distal ends in the form of a Y so as to respectively receive a part of rocker 7 and a part of support part 1 in the space separating the two branches of the Y, thereby enabling assembly to be performed by means of corresponding pins. The parts of the rocker and of support part 1 each comprise a bore designed to receive a pin forming an assembly point of rod 8.

In the particular example of FIGS. 4 and 5, for rod 8, the pin at the level of the rocker is fixed with respect to rod 8, enabling swivelling of the rocker around this pin. The pin at the level of support part 1 is fixed with respect to support part 1, enabling swivelling of rod 8 around this pin. For the absorbing system, it is fitted swivelling on the pin of pivot link 2 and on the pin acting as assembly point on the rocker, said assembly pin being fixed with respect to the rocker.

Figure 8:
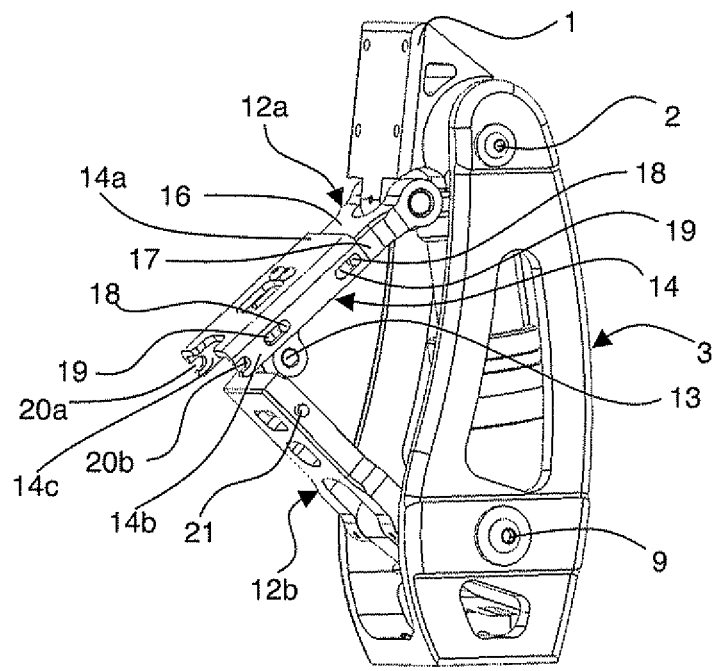
FIG. 8 illustrates a view in three dimensions in which the rod is disengaged.
Figure 9:
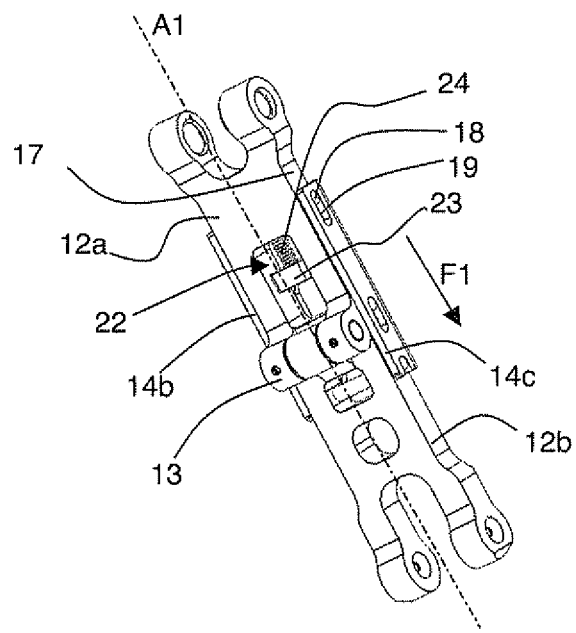
FIG. 9 illustrates the rod used according to a particular embodiment.

According to a particular embodiment, rod 8 can be arranged so as to occupy a first position in which the swivelling movement of support part 1 with respect to leg 3 is transmitted to rocker 7, and a second position (FIG. 8) in which said movement is not transmitted to rocker 7 (FIGS. 4 and 5). This can for example be achieved by a rod 8, as illustrated in FIG. 9, comprising a first plate 12a (or element) mounted on support part 1 (FIGS. 4 to 8) and a second plate 12b (or element) mounted on rocker 7. First plate 12a forms a hinge 13 with second plate 12b. In other words, first plate 12a is pivotally mounted on second plate 12b to prevent transmission of a movement of support part 1 to rocker 7, should such a movement take place. Hinge 13 can be formed on the median of rod 8, perpendicularly to the longitudinal axis A1 of said rod 8.

This rod 8 with two positions presents an advantage when the prosthesis is used for skiing. In a first position, the skier can in fact solicit the prosthesis when descending a slope, and when he/she embarks on a ski lift, the prosthesis can move to the second position of rod 8 enabling the skier to sit down without difficulty on the seat of the ski lift as the absorbing system 4 is deactivated.

Rod 8 preferably comprises latching means arranged so as to prevent swivelling of first plate 12a with respect to second plate 12b in the first position and to enable said swivelling in the second position.

FIGS. 5 to 9 illustrate a particular embodiment of such latching means. The latter can comprise a mounting plate 14 fitting sliding on one of plates 12a, 12b, preferably on the rear surface of the prosthesis, in a plane parallel to the plane of the associated plate. At one end, mounting plate 14 preferably comprises first engagement means 15a collaborating in the first position with second engagement means 15b of the other plate to latch the first and second plates to one another. In the first position, the first and second plates are deprived of relative movements with respect to one another. In other words, the two plates behave as a monoblock part. In the second position, first plate 12a can swivel with respect to second plate 12b, for example at the level of hinge 13, so as not to transmit the movement from support part 1 to rocker 7, this enabling the stresses imposed on absorbing system 4 to be relaxed.

In a particular example of FIGS. 4 to 9, mounting plate 14 comprises a base 14a joining two parallel opposite sides walls 14b, 14c, oriented in the longitudinal direction (axis A1 in FIGS. 7 and 9) of rod 8 in the first position. A transverse dimension of base 14a is larger than the transverse dimension of first plate 12a so that base 14a snugly follows a main surface 16 of said first plate 12a. In the example, main surface 16 is substantially parallel to the plane of first plate 12a. The two opposite sides walls 14b, 14c each respectively snugly follow an edge 17 of the first plate 12a (edge substantially perpendicular to surface face 16). Edges 17 of first plate 12a each comprise at least one protrusion 18 substantially perpendicular to said edge 17. Each protrusion 18 collaborates with an aperture 19 made in corresponding side wall 14b, 14c of mounting plate 14. According to the particular embodiment, each edge 17 comprises two protrusions and each side wall comprises two corresponding apertures. The apertures and protrusions on the one hand enable the mounting plate to be kept mounted on first plate 12a, and on the other hand enable the travel of mounting plate 14 to be limited with respect to first plate 12a. In other words, a protrusion passes at least partially through the associated aperture to form a stop for movement of mounting plate 14 with respect to the first plate. The transverse dimensions of the protrusion are substantially equal to the transverse dimensions of the aperture perpendicularly to the longitudinal axis of the sides walls.

In order to block first plate 12a with second plate 12b, mounting plate 14 can comprise two recesses 20a, 20b forming the first engagement means, at an end directed towards second plate 12b (FIG. 8), each recess being made at the level of a side wall of mounting plate 14 and running along the longitudinal axis of mounting plate 14. In the first position, each recess 20a, 20b collaborates with a corresponding lug 21 of second plate 12b which is then housed in the associated recess. lug 21, forming the second engagement means, is formed salient from an edge of second plate 12b.

Mounting plate 14 is preferably constantly biased in the direction of the plate on which it is not fitted, for example by biasing element such as a spring. This embodiment can be implemented as for example in FIG. 9 in which first plate 12a comprises a through opening 22 made at the level of one of its surfaces perpendicularly to the plane of said first plate 12a. The base of the mounting plate then comprises a protuberance 23 able to move in opening 22, between the two sides walls 14b, 14c, said protuberance 23 then being connected to an inner surface of the opening by a spring 24 so as to stress movement of mounting plate 14 in an opposite direction to the first element (in the direction of arrow F1 in FIG. 9). In FIG. 9 spring 24 is a compression spring and the latter connects protuberance 23 to a distal inner surface of the opening of hinge 13. The person skilled in the art can naturally also use a tension spring secured to the protuberance and to an inner face of the proximal opening of hinge 13.

The user of the prosthesis can thus pull on the mounting plate in an opposite direction to arrow F1 to disengage the recesses from their respective lugs and to move the prosthesis to the second position of rod 8. To be able to return to the first position, the user can perform the reverse action. In preferential manner, the ends of sides walls 14b, 14c of mounting plate 14 at the level of the recesses and facing the associated lugs each comprise a bevel enabling automatic latching of the recesses with the lugs when the user resumes a standing position. Rod 8 tends to return to the first position, when returning on the feet up position, and the bevel then comes into contact with an associated lug, naturally pushing mounting plate 14 in an opposite direction to arrow F1 until engagement is achieved. In other words, in general manner, the first and second engagement means can be formed in such a way as to engage automatically when extension of the prosthesis takes place when the latter is in the second position.

This involves an example embodiment, the person skilled in the art naturally being able to modify the assembly, for example by reversing assembly of the first plate and of the second plate respectively on the rocker and on the support part.

According to a development, the absorbing system comprises a jack. The jack is preferably of oleo-pneumatic type. It preferably enables distinct adjustment of its compression force and of its speed of expansion. In other words, the jack can comprise distinct means for adjusting its compression force and its speed of expansion. For example, the speed of expansion can be adjusted to provide a softer return from the flexion position to the extension position. This enables, in particular, the lower limb to be adjusted according to the level and the desire of the user.

By extension, when referring to a lower limb prosthesis, the element for receiving a thigh stump, the support part and the leg are mechanical elements enabling an amputated person, for example a skier, to find his bearings on both of his lower limbs, and to perform functions close to that of a real lower limb under particular conditions such as the triple flexion position (hip, knee, ankle). For this, the pins referred to above (pivot link pin, assembly pins of the rod on the support part and on the rocker, assembly pin of the absorbing system on the rocker and swivel pin of the rocker), are all preferably substantially parallel to one another.

Figure 10:
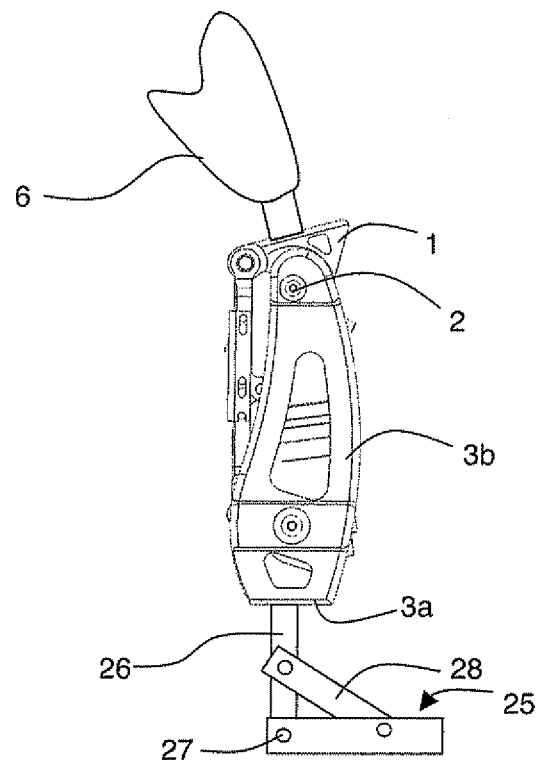
FIG. 10 illustrates a particular embodiment of a lower limb.

As illustrated in FIG. 10, the prosthesis can further comprise a foot 25 fitted on one end of leg 3 opposite support part 1, for example on a rod 26 of the leg fixed to the main body 3a, 3b, 3c opposite the support part. Foot 25 is pivotally mounted on said leg 3, the axis of pivoting then being substantially parallel to the pin of pivot link 2 forming the joint. Rod 26 can be assembled on foot 25 by a pin 27 at the level of the area called the instep. Rod 26 can be connected by means of a jack 28 with one end of foot 25 opposite rod 26. The use of jack 28 at the level of the foot enables a compensation of the flexion of the prosthesis to be obtained at the level of the joint by a dorsal flexion of the foot.

According to an alternative embodiment (not shown), a sole is fitted on a bottom surface of the foot, said sole taking a shape designed to collaborate with a binding for a ski boot.

In the particular case of snow sports, the amplitude of movement provided by such a prosthesis enables the user to adapt to any type of skiing or snow surfing.

Support part 1 can comprise a preferably flat surface opposite the joint (pivot link 2) designed for fixing element for receiving 6 a thigh stump. The element for receiving can comprise a plate, for example fixed to said surface by screws. The plate of the element for receiving is itself fixed to a receptacle, for example made from carbon fiber, shaped in the same way as the stump of the user's lower limb.

Tests carried out on this prosthesis using a jack as absorbing system have enabled it to be shown that, with an angle of flexion $\alpha$ of 155 degrees, the force exerted by the jack is about 2200N, whereas with an angle of flexion $\alpha$ of 110 degrees, the force Fjack exerted by the jack of the absorbing system is about 3340N. In other words, compared with the prior art, the prosthesis described above enables a substantially constant absorbing force to be kept on the jack whatever the angle of flexion at the knee, in particular due to the use of a restoring force. Thus, unlike the prior art, this prevents absorbing from being lost and procures an improved user comfort approaching that of a valid lower limb.

Apart from the fact that the prosthesis is more robust, keeping a substantially constant force at the level of the absorbing system whatever the angle of flexion $\alpha$ of the prosthesis enables enhanced performances to be achieved throughout a ski run. This in particular makes it possible to press on the prosthesis while at the same time keeping a high level of control of the ski even when pressing is unilateral.

The invention claimed is:

1. A prosthesis for a lower limb, comprising:
   an element for receiving a thigh stump fitted on a support part;
   a leg connected to said support part by a pivot link forming a knee joint to enable flexion or extension of the leg with respect to the element for receiving;

an absorbing system to absorb the flexion or extension efforts, a first end of the absorbing system being fitted on a pin of the pivot link and a second end of the absorbing system being fitted to a first end of a rocker that is pivotally fitted on the leg; and a rod disposed such that a first end of the rod is mounted on a second end of the rocker, and a second end of the rod is mounted on the support part.

2. The prosthesis according to claim 1, wherein the rod is arranged so as to occupy a first position in which a swiveling movement of the support part with respect to the leg is transmitted to the rocker, and a second position in which said movement is not transmitted to the rocker.

3. The prosthesis according to claim 2, wherein the rod comprises a first plate mounted on the support part and a second plate mounted on the rocker, said first plate forming a hinge with the second plate, and wherein the rod comprises latching means arranged so as to prevent swiveling of the first plate with respect to the second plate in the first position and to enable the swiveling of the first plate with respect to the second plate in the second position.

4. The prosthesis according to claim 3, wherein the latching means comprises a mounting plate mounted sliding on one of the plates, said mounting plate comprising first engagement means collaborating with second engagement means of the other plate to latch the first and second plates to one another in the first position.

5. The prosthesis according to claim 4, wherein the mounting plate is constantly biased in the direction of said other plate by a biasing element.

6. The prosthesis according to claim 1, wherein the absorbing system comprises a jack.

7. The prosthesis according to claim 1, comprising a foot fitted at one end of the leg, opposite the support part, said foot being pivotally mounted on said leg, the axis of pivoting being substantially parallel to the pin of the pivot link forming the joint.

8. The prosthesis according to claim 7, wherein a sole is fitted on a bottom surface of the foot, said sole taking a shape designed to collaborate with a binding for a ski boot.

9. A prosthesis for a lower limb, comprising:
a support part;
an element mounted to the support part and configured to receive a thigh stump;
a leg pivotally connected to the support part at a pivot point to form a knee joint, the knee joint providing flexion and extension of the leg relative to the element;
a rocker having first and second ends and being pivotally connected to the leg;
a shock absorbing system having a first end connected to the support part at the pivot point, and a second end pivotally connected to the first end of the rocker, the shock absorbing system being operable to absorb forces during flexion and extension;
a rod having a first end pivotally connected to the second end of the rocker, and a second end pivotally connected to the support part.

10. The prosthesis according to claim 9, wherein the rod is operable to move between a first position in which a swiveling movement of the support part with respect to the leg is transmitted to the rocker, and a second position in which the movement is not transmitted to the rocker.

11. The prosthesis according to claim 10, wherein the rod comprises a first plate pivotally connected to the support part, and a second plate pivotally connected to the rocker, the first plate having a hinge connection with the second plate, and the rod comprises a latch configured to prevent swiveling of the first plate relative to the second plate when the rod is in the first position, and to enable the swiveling movement of the first plate relative to the second plate when the rod is in the second position.

12. The prosthesis according to claim 11, wherein the latch comprises a mounting plate slidingly mounted on one of the first and second plates, the mounting plate comprising a first engagement member cooperating with a second engagement member of the other of the first and second plates to latch the first and second plates to one another in the first position.

13. The prosthesis according to claim 12, wherein the mounting plate is biased toward the other of the first and second plates by a biasing element.

14. The prosthesis according to claim 9, wherein the shock absorbing system comprises a jack.

15. The prosthesis according to claim 14, wherein the jack is an oleo-pneumatic jack.

16. The prosthesis according to claim 9, further comprising a foot pivotally mounted to an end of the leg that is opposite an end of the leg that is connected to the support part, wherein an axis of pivoting for the foot is substantially parallel to a pivot pin defining the pivot point of the knee joint.

17. The prosthesis according to claim 16, wherein a sole is fitted on a bottom surface of the foot, said sole taking a shape designed to collaborate with a binding for a ski boot.

18. The prosthesis according to claim 9, wherein the rod is connected to the support part at a location spaced apart from the pivot point.

19. The prosthesis according to claim 9, wherein the shock absorbing member and the rod are connected to the rocker at locations spaced apart from a pivot connection point of the leg to the rocker.

* * * * *